United States Patent [19]

Disdier et al.

[11] 4,431,442

[45] Feb. 14, 1984

[54] 2-METHYLENESUCCINAMIC ACID COMPOUNDS AS PLANT GROWTH REGULANTS

[75] Inventors: André Disdier, Villeurbanne; Guy Borrod, Lyons; Stéphane Trinh, Champagne au Mont d'Or, all of France

[73] Assignee: Rhone-Poulenc Agrochimie, Lyons, France

[21] Appl. No.: 231,721

[22] Filed: Feb. 5, 1981

[30] Foreign Application Priority Data

Feb. 18, 1980 [FR] France ................................ 80 03876

[51] Int. Cl.$^3$ .................. A01N 37/44; C07C 101/453
[52] U.S. Cl. ........................................ 71/111; 71/115;
560/43; 562/456; 562/433; 260/501.11
[58] Field of Search .................. 560/43; 562/456, 433;
71/111, 115; 260/501.11

[56] References Cited

U.S. PATENT DOCUMENTS

| | | | |
|---|---|---|---|
| 3,097,944 | 7/1963 | Riddell et al. | 71/95 |
| 3,228,972 | 1/1966 | Schwartz | 560/43 |
| 3,375,158 | 3/1968 | Neighbors | 560/43 |
| 3,510,509 | 5/1970 | Neighbors | 560/22 |
| 4,125,398 | 11/1978 | Roth | 71/115 |
| 4,216,008 | 8/1980 | Weigele et al. | 71/111 |
| 4,246,429 | 1/1981 | Van Daele | 71/115 |
| 4,284,427 | 8/1981 | Akahira et al. | 71/111 X |

FOREIGN PATENT DOCUMENTS 942753 2/1974 Canada .

OTHER PUBLICATIONS

Zilkha et al., J. Org. Chem., 28(8), 2007–2009 (1963).
Karanor et al., Chem. Absts. 93, 63475(z) 1980.

*Primary Examiner*—Bernard Helfin
*Attorney, Agent, or Firm*—Burns, Doane, Swecker & Mathis

[57] ABSTRACT

2-Methylenesuccinamic acid compounds are useful plant growth regulants, e.g., are useful in regulating the growth of soya crops.

27 Claims, No Drawings

2-METHYLENESUCCINAMIC ACID COMPOUNDS AS PLANT GROWTH REGULANTS

BACKGROUND OF THE INVENTION

Field of the Invention

The present invention relates to compositions of matter for regulating plant growth, with certain 2-methylenesuccinamic acid derivatives comprising the active ingredient thereof, and also to methods for regulating plant growth comprising application to a plant locus of an effective amount of such derivatives. The invention further relates to novel 2-methylenesuccinamic acid compounds, per se, which can be used as the active ingredient in the compositions and the treatments according to the invention, and also to the preparation of such novel derivatives.

In the text of the present patent application, the expressions "for regulating growth" and "growth regulators" are to be understood as having their common meaning in the French language, which corresponds to "growth substances" in the Anglo-Saxon literature, the word "growth" relating to the production of living material and not simply to the modification of the size of plants. "Growth regulators" will therefore be understood hereafter as connoting products which are capable of modifying the physiology of plants in a variety of manners.

2. Description of the Prior Art

In the field of agriculture, it is of course a permanent aim of agronomists to improve crop yields, especially in the case of crops which are significantly economically important, such as, e.g., a soya crop. One measure with a view towards achieving this aim is to combat the parasites and predators of these crops by destroying the weeds and the harmful insects in the crops using selective weed killers and suitable insecticides, and also to combat the fungal diseases in such crops using suitable antifungal products.

Independently of these commonly employed measures, it is very desirable to exert action or influence on the crops themselves in order to stimulate or selectively orient their physiological development, such as to improve the yields therefrom.

SUMMARY OF THE INVENTION

Accordingly, a major object of the present invention is the provision of improved agronomically effective means permitting an increase in crop yields by affecting the growth pattern, rate, etc., of the plants, in particular as regards soya.

Briefly, the above and other objects of the invention are attained by regulating crop plant growth with an agronomically effective amount of at least one compound having the structural formula I:

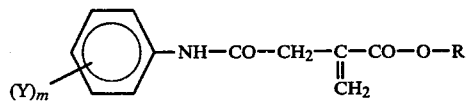

(I)

in which: R represents a hydrogen atom, an alkyl radical containing from 1 to 16 carbon atoms, an alkenyl radical containing from 3 to 15 carbon atoms or an alkynyl radical containing from 3 to 5 carbon atoms, Y represents a halogen atom or an alkyl radical containing from 1 to 4 carbon atoms and m is an integer from 0 to 5 ($0 \leq m \leq 5$), it being understood that if m is greater than 1, the substituents Y can be identical or different, or at least one salt of such compound.

By "salt of the compound having the formula I" there is intended the salt formed by the acid corresponding to the formula I, in the case where R represents a hydrogen atom, with an inorganic or organic base. In like manner, the expression "salt of the compound of the formula III or IIIa" will connote "salt formed by the acid corresponding to this formula with an inorganic or organic base".

DETAILED DESCRIPTION OF THE INVENTION

More particularly according to this invention, the salts of the active ingredient of the formula I are represented in general terms by the formula:

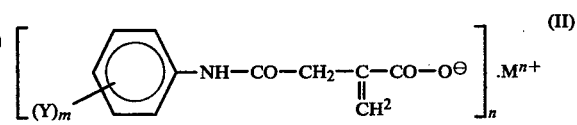

(II)

in which: M represents an inorganic or organic cation of valency n, and Y and m have the same meaning as in the formula I.

The alkali metal or alkaline earth metal salts, and also the amine salts, are preferred salts of the compound of the formula I which are useful plant growth regulators according to the invention. The amine salts correspond to the formula II in which n is equal to 1 and $M^{n+}$ represents the cation of the formula:

in which $R_1$, $R_2$ and $R_3$, which are identical or different, each represent a hydrogen atom or an optionally substituted alkyl radical.

The alkali metal or alkaline earth metal salts are conventionally obtained by simple salification of the acid corresponding to the formula I (in the case where R represents the hydrogen atom) using a suitable base, or by means of a double decomposition reaction between a salt of the said acid and another salt containing the desired action.

The amine salts are typically obtained by reacting the acid corresponding to the formula I (in the case where R represents the hydrogen atom) with a suitable primary, secondary or tertiary amine, e.g., with ethanolamine. The use of long-chain amines of the fatty amine type makes it possible to obtain water-soluble and/or lipid-soluble salts.

The invention relates more particularly to compositions for regulating plant growth, in which at least one compound corresponding to the above-mentioned formula I in which m is equal to 0, 1, 2 or 3, Y represents a halogen atom and R has the same meaning as in the said formula, or at least one salt of this compound, comprises the active ingredient.

Among such compounds, preferred sub-genera include those corresponding to the following formulae III and IIIa:

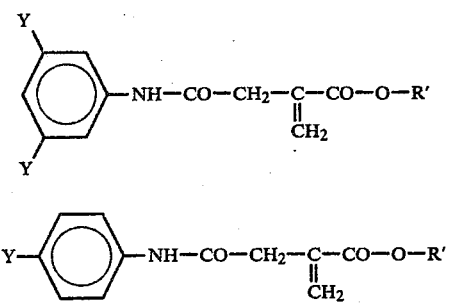

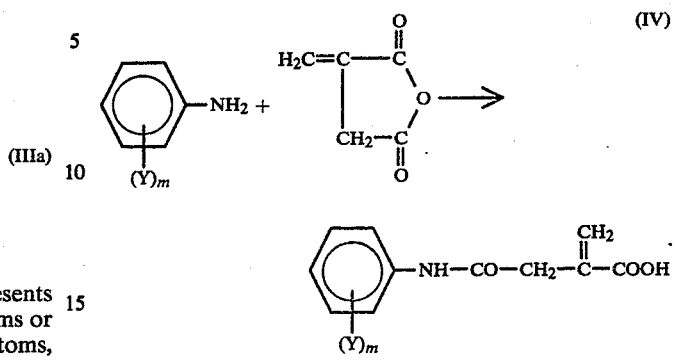

in which Y represents a halogen atom and R' represents an alkyl radical containing from 1 to 8 carbon atoms or an alkenyl radical containing from 3 to 5 carbon atoms, and also the amine salts of these compounds (especially the alkanolamine salts).

Among the compounds noted above, excellent results have been obtained by using, as the active ingredient in the compositions according to the invention, the compounds corresponding to the formula III in which Y represents a halogen atom and R represents an alkenyl radical containing from 3 to 5 carbon atoms, such as, e.g., the allyl radical.

Certain of the compounds circumscribed by the formula I are per se known to this art; thus:

*J. Org. Chem.*, Volume 28, August 1963, pages 2,007–9, describes N-phenyl-2-methylenesuccinamic acid;

French Pat. No. 1,310,442 claims N-phenylitaconimides as herbicides, these compounds being different from the compounds according to the invention, but being prepared from N-arylitaconamic acids which are themselves obtained by reacting an aromatic amine with itaconic anhydride; and Belgian Pat. No. 732,138 and its British counterpart, Pat. No. 1,209,005 claim N-(3,5-dichlorophenyl)-itaconimide as an antimicrobial and antifungal agent, this compound being different from the compounds according to the invention, but being prepared from N-(3,5-dichlorophenyl)-itaconic acid.

The literature thus describes certain of the acids corresponding to the formula I (in the case where R represents hydrogen). However, no reference either discloses or suggests the possibility that these acids might be active in the regulation of plant growth, or even any use of these acids as the active ingredient in compositions for agricultural use. Cf. U.S. Pat. Nos. 3,097,944, 3,375,158, 3,510,509 and 4,125,398; French Pat. Nos. 1,310,442 and 2,330,317; and British Pat. No. 1,209,005.

In addition to the compositions mentioned above, the invention also relates, as new compounds, to the compounds corresponding to the formula I and their salts corresponding to the formula II, with the exclusion, however, of the acids corresponding to the formula I (in which R represents the hydrogen atom). It relates more particularly to those compounds in which m is equal to 0, 1, 2 or 3 and Y represents a halogen atom, and also to the amine salts of such compounds.

Preferably, the invention relates to the novel compounds corresponding to the formulae III and IIIa, and more particularly to the compounds corresponding to the formula III in which R' represents an alkenyl radical containing from 3 to 5 carbon atoms, such as the allyl radical.

The compounds according to the formula I in which R represents a hydrogen atom can be obtained by reacting an aniline with itaconic anhydride in accordance with the following equation:

in which Y and m have the same meaning as in the formula I.

The reaction is carried out in an anhydrous medium, advantageously in an inert solvent (i.e., chemically inert towards the reactants and reaction products, under the operating conditions), at a temperature between about 20° and 150° C.

Suitable solvents which may be mentioned are polar or non-polar organic solvents, such as aromatic hydrocarbons (such as benzene, toluene, xylenes and chlorobenzene), aliphatic hydrocarbons (such as hexane, heptane, cyclohexane and methylcyclohexane), chlorinated aliphatic hydrocarbons (such as dichloroethane, dichloroethylene, carbon tetrachloride and perchloroethylene), ethers (such as dioxane, tetrahydrofuran, diethyl ether and diisopropyl ether), ketones (such as acetone, methyl ethyl ketone and methyl isobutyl ketone) or nitriles (such as acetonitrile).

Upon completion of the reaction, the formed acid IV can be isolated from the reaction medium by any means in and of itself known, such as, e.g., by distillation of the solvent or by crystallization of the product from the reaction medium, and then, if necessary, this acid is purified by customary methods, such as recrystallization from a suitable solvent or liquid phase chromatography.

The compounds according to the formula I in which R represents an alkyl, alkenyl or alkynyl radical can be obtained from the acids according to the formula IV by esterification, using a suitable alcohol, in accordance with the following equation:

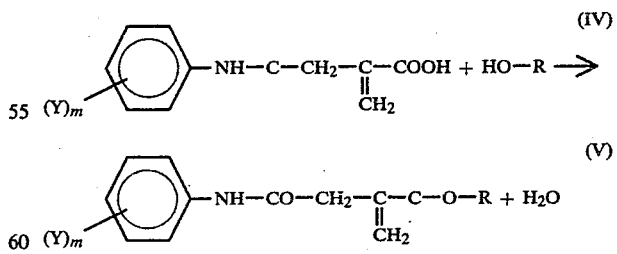

in which Y and m have the same meaning as in the formula I and R represents an alkyl radical containing from 1 to 16 carbon atoms, an alkenyl radical containing from 3 to 15 carbon atoms or an alkynyl radical containing from 3 to 5 carbon atoms.

The reaction is carried out in an anhydrous medium, at a temperature between 50° and 160° C., in the presence of a catalyst of the Lewis acid type, such as, e.g., hydrochloric acid, sulfuric acid and aryl- or alkyl-sulfonic acids (in particular methanesulfonic acid and p-toluenesulfonic acid).

Advantageously, the reaction is carried out in an inert solvent, such as, e.g., those used in the preparation of the acid of the formula IV, which have been listed above. This reaction can also be carried out in an excess of alcohol of the formula R—OH, which then serves both as a reactant and as a solvent, with or without the combined use of another solvent.

To facilitate the reaction by displacing the equilibrium towards the right, the water formed is advantageously removed by azeotropic distillation from the ternary mixture solvent/alcohol/water or the binary mixture alcohol/water.

Upon completion of the reaction, the products formed are isolated by any means per se known to the art, such as, e.g., by filtration, by distillation of the solvent or by crystallization of the product from the reaction medium, and then, if necessary, same are purified in accordance with the customary methods.

The compounds according to the formula I in which R represents an alkyl, alkenyl or alkynyl radical can also be prepared in accordance with a second process, which consists of reacting a salt of the acid of the formula IV (preferably a sodium or ammonium salt) with a halide of the formula XR, in which R has the same meaning as above and X represents a halogen atom (preferably a bromine or chlorine atom). The reaction is carried out in organic or aqueous-organic solvent medium, at a temperature which is typically between 20° and 100° C. The solvents mentioned above in the case of the preparation of the acid of the formula IV may be mentioned as solvents which can be used. Upon completion of the reaction, the products formed are isolated by any known means, such as those mentioned above, and then, if necessary, they are purified by the customary methods.

The alkali metal, alkaline earth metal or ammonium salts of the acid of the formula IV can be obtained by reacting a base, such as sodium hydroxide or ammonia, with this acid, generally in an aqueous or aqueous-organic medium, at or above ambient temperature. The amine salts of the acid of the formula IV can be obtained by reacting the said acid with a suitable amine, under the action of heat, in an organic or aqueous-organic solvent medium.

In order to further illustrate the present invention and the advantages thereof, the following specific examples are given, it being understood that same are intended only as illustrative and in nowise limitative. The compounds described in Examples 1 to 14 were identified by nuclear magnetic resonance spectrometry (NMR), the spectra having been determined at 60 megahertz in CCl$_4$ or CDCl$_3$, using hexamethyldisiloxane as the internal reference.

EXAMPLE 1

Preparation of N-(3,5-dichlorophenyl)-2-methylenesuccinamic acid (compound No. 1)

Itaconic anhydride (33.6 g; 0.3 mol) was dissolved in toluene (300 ml) at about 60° C. and a solution of 3,5-dichloroaniline (48.6 g; 0.3 mol) in toluene (200 ml) was slowly poured into the resulting solution. The appearance of a precipitate was observed. The reaction mixture was stirred, at ambient temperature (15° to 25° C.), for two hours.

The product formed was filtered off and then dried. N-(3,5-Dichlorophenyl)-2-methylenesuccinamic acid (66.6 g) melting at 185° C. was thus obtained, the yield being 81%.

| | Elementary composition | |
|---|---|---|
| | calculated | found |
| C % | 48.17 | 48.00 |
| H % | 3.28 | 3.11 |
| N % | 5.10 | 5.22 |
| Cl % | 25.91 | 25.81 |

The itaconic anhydride and the aniline used as starting materials were commercially available, off-the-shelf items.

EXAMPLE 2

Preparation of allyl N-(3,5-dichlorophenyl)-2-methylenesuccinamate (compound No. 2)

N-(3,5-Dichlorophenyl)-2-methylenesuccinamic acid (27.4 g; 0.1 mol), allyl alcohol (200 ml) and concentrated sulfuric acid (1 ml) were mixed at ambient temperature (15° to 25° C.) until a solution was obtained. This solution was then heated under reflux for 2 hours, the mixture allyl alcohol/water being distilled. Throughout the distillation, allyl alcohol was added to the solution so as to replace that fraction removed by distillation. After cooling to ambient temperature, the excess allyl alcohol was evaporated off under a partial vacuum from a water pump. The residue was dissolved in methylene chloride (200 ml) and the resulting solution was washed with water (200 ml), then with a 5% strength solution of sodium bicarbonate (100 ml) and finally with water (200 ml). After drying over anhydrous sodium sulfate and removing the methylene chloride by evaporation, the residue was recrystallized from diethyl ether (150 ml), and allyl N-(3,5-dichlorophenyl)-2-methylenesuccinamate (14.8 g) melting at 99° C. was thus obtained, the yield being 47.1%.

| | Elementary composition | |
|---|---|---|
| | calculated | found |
| C % | 53.50 | 53.51 |
| H % | 4.14 | 4.03 |
| N % | 4.45 | 4.48 |
| Cl % | 22.61 | 22.19 |

The preparation of N-(3,5-dichlorophenyl)-2-methylenesuccinamic acid is described in Example 1.

EXAMPLES 3 and 4

By following the procedure of Example 2, using N-(3,5-dichlorophenyl)-2-methylenesuccinamic acid and a suitable alcohol as the starting materials, the following compounds were prepared:

Methyl N-(3,5-dichlorophenyl)-2-methylenesuccinamate (compound No. 3) melting at 113°–114° C.

Isopropyl N-(3,5-dichlorophenyl)-2-methylenesuccinamate (compound No. 4) melting at 93° C.

EXAMPLE 5

Preparation of n-butyl N-(3,5-dichlorophenyl)-2-methylenesuccinamate (compound No. 5)

N-(3,5-Dichloropheny)-2-methylenesuccinamic acid (11 g) was dissolved in a solution of sodium hydroxide (1.6 g) in water (50 ml), and the sodium salt of this acid was thus formed.

A solution of n-butyl bromide (5.5 g) in ethanol (100 ml) was added to the resulting solution. The reaction mixture obtained was heated for 16 hours at the reflux temperature of the mixture water/ethanol. The oil formed was then extracted with methylene chloride (200 ml). After drying over anhydrous sodium sulfate and evaporating off the solvent, an oil was obtained which crystallized at ambient temperature. The crude product obtained was recrystallized from cyclohexane (100 ml). n-Butyl N-(3,5-dichlorophenyl)-2-methylenesuccinamate (2.8 g) melting at 69.5° C. was thus obtained. Yield: 21.2%.

EXAMPLE 6

By following the procedure of Example 5, using the same acid and n-hexyl bromide as the starting materials, n-hexyl N-(3,5-dichlorophenyl)-2-methylenesuccinamate (compound No. 6) melting at 60° C. was obtained. Yield: 13.3%.

EXAMPLE 7

Preparation of ethanolamine N-(3,5-dichlorophenyl)-2-methylenesuccinamate (compound No. 7) having the structural formula:

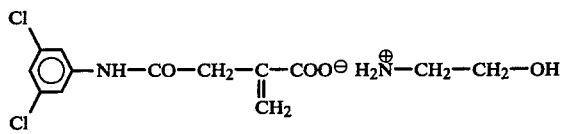

N-(3,5-Dichlorophenyl)-2-methylenesuccinamic acid (13.7 g), ethanolamine (3.05 g) and ethanol (50 ml) were mixed and the mixture obtained was heated for 30 minutes at the reflux temperature of the ethanol. After evaporating to dryness, a very viscous crude product was obtained which was dried at 50° C. under a pressure of $5.10^{-2}$ mm Hg.

The desired product (16.5 g) was thus obtained in the form of a water-soluble viscous liquid. Yield: 98.5%.

EXAMPLES 8, 9 and 10

By following the methods described in Examples 1, 2 and 7, respectively, using the appropriate starting materials, the following compounds were prepared:

N-(4-Chlorophenyl)-2-methylenesuccinamic acid (compound No. 8) melting at 182°–183° C. Yield: 95%.

Allyl N-(4-chlorophenyl)-2-methylenesuccinamate (compound No. 9) melting at 82.3° C. Yield: 17%.

Ethanolamine N-(4-chlorophenyl)-2-methylenesuccinamate (compound No. 10), obtained in the form of a water-soluble viscous liquid. Yield: 99.2%.

EXAMPLES 11 and 12

By following the methods described in Examples 1 and 2, respectively, using the appropriate starting materials, the following compounds were prepared:

N-(3,4-Dichlorophenyl)-2-methylenesuccinamic acid (compound No. 11) melting at 158.5° C.

Methyl N-(3,4-dichlorophenyl)-2-methylenesuccinamate (compound No. 12) melting at 111.7° C. Yield: 42.4%.

EXAMPLES 13 and 14

The following the methods described in Examples 1 and 7, respectively, using the appropriate starting materials, the following compounds were prepared:

N-(4-Methylphenyl)-2-methylenesuccinamic acid (compound No. 13) melting at 174°–175° C. Yield: 94%.

Ethanolamine N-(4-methylphenyl)-2-methylenesuccinamate (compound No. 14). Viscous liquid. Yield: 100%.

The properties of the compounds according to the invention in the regulation of plant growth were demonstrated by the experiments described in Examples I to III. In these experiments, the term solution is to be understood as meaning either an aqueous solution, in the case where the active ingredient is water-soluble, or, in the opposite case, an aqueous dispersion or emulsion obtained by diluting, with water, either a wettable powder comprising 20% by weight of active ingredient, or an emulsifiable concentrate containing about 200 g/liter of active ingredient, respectively. These experiments were carried out either in a greenhouse or in an open field, with the leaves of the plants, such as bean and soya plants, being treated with a solution in which the content of active ingredient to be tested varied from 0.01 g/liter to 20 g/liter. The biometric and morphological changes, over time, of the treated plants were then observed and compared with those of control plants treated under the same conditions with a solution which did not contain any active ingredient.

EXAMPLE I

Greenhouse experiment on beans (*Phaseolus vulgaris*) of the Contender variety, post-emergence treatment A solution of the ingredient to be tested was prepared, at the desired concentration, by diluting, with water, an emulsifiable concentrate having the following composition:

| | |
|---|---|
| Ingredient to be tested | 200 g |
| Wetting and emulsifying agent (acid phosphate of a 9:1 ethylene oxide/nonylphenol condensate) | 100 g |
| Solvent (cyclohexanone) q.s.p. | 1 liter |

Bean seeds were sown in 9×9×9 cm pots filled with light agricultural earth and were then covered with a half-centimeter thick layer of earth, and the pots were maintained in a greenhouse at ambient temperature, under 70% relative humidity, and were watered by subirrigation.

When the bean plants reached the stage of two developed primordial leaves and a terminal bud which was ready to open, their foliage was treated by spraying same with the previously prepared solution, at a rate of about 500 liters/hectare of solution, for doses of active ingredient ranging from 1 to 8 kg/hectare.

The treated pots were subsequently placed in troughs which were designed to receive moistening water by subirrigation, and were then maintained for 35 days at ambient temperature, under 70% relative humidity. During this period, the results were observed in the case of the plants treated with the active ingredient according to the invention, and such results were compared with those obtained in the case of control plants treated with a solution which did not contain active ingredient.

Under these conditions, it was observed that the plants treated with the compounds according to the invention exhibited the following effects, as compared with the untreated controls:

Compound No. 1:

At 1 and 2 kg/hectare: 45% reduction in size (i.e., the average height of the treated plants was equal to 55% of that of the untreated control plants).

At doses of 4 and 8 kg/hectare: 60% reduction in size and very significant development of side shoots from axially buds.

Compound No. 2:

At 8 kg/hectare: 45% reduction in size, and at 4 kg/hectare: 30% reduction in size.

At 8, 4, 2 and 1 kg/hectare: very significant development of side shoots from the axillary buds, resulting in a very considerable increase in the number of ramifications, and slight deformation of the newly-formed trifoliate leaves.

Compound No. 3:

At 8 and 4 kg/hectare: about 25% reduction in size and slight deformation of the trifoliate leaves.

Compound No. 4:

At 4 and 8 kg/hectare: about 25% reduction in size and slightly greater development of side shoots from the axillary buds than in the case of the control plants.

Compound No. 5:

At 8 and 4 kg/hectare: significant reduction in size (i.e., between 30 and 60%) and significant development of side shoots from the axillary buds.

At 2 kg/hectare: slight development of side shoots.

Compound No. 6:

At 8 and 4 kg/hectare: about 60% reduction in size and very significant development of side shoots from the axillary buds.

At 2 kg/hectare: 40% reduction in size, and at 1 kg/hectare: 30%.

Compound No. 7:

At 8 kg/hectare: significant reduction in size and significant development of side shoots from the axillary buds, with slight deformation of the trifoliate leaves.

At 4 kg/hectare: slight reduction in size (i.e., less than 30%) and slight development of side shoots from the axillary buds.

Compound No. 8:

At 8 kg/hectare: slight reduction in size and significant development of side shoots from the axillary buds, with slight deformation of the trifoliate leaves.

Compound No. 10:

At 8, 4 and 2 kg/hectare, significant deformation of the trifoliate leaves (leaves with a spoon-like appearance).

Compound No. 12:

At 8 kg/hectare: 35% reduction in size and slight development of side shoots from the axillary buds.

EXAMPLE II

Greenhouse test on beans of the Contender variety, pre-emergence treatment

The procedure of the preceding Example I was followed, except that the soil was treated with active ingredient immediately after the bean seeds had been sown.

Under these conditions, the plant corresponding to the treatment with compound No. 2, at a dose of 8 kg/hectare, exhibited a very significant development of the side shoots, compared with the control.

EXAMPLE III

Open-field experiment on soya (Glycine max.) of the Amsoy-71 variety

On July 27th, soya seeds were sown in a 3×10 m plot in three parallel rows, each 10 m long, spaced 0.50 m apart.

On August 20th, when the soya plants were at the stage of two fully-open trifoliate leaves, the plants in two of these rows were treated by spraying them with a solution prepared by diluting, with water, to the desired concentration, the same emulsifiable concentrate as used in Example I.

This solution was applied to the soya plants until they were dripping wet, such that the dose of active ingredient applied to two rows was, respectively, 1 kg/hectare (first row) and 2 kg/hectare (second row), the third row not being subjected to any treatment and used as a control.

On December 18th, the number of ramifications on the treated plants was evaluated, the pods formed were collected and the results were compared with those obtained in the case of the control plants in the third row.

Under these conditions, it was observed that the results obtained by using compound No. 2 as the active ingredient were as follows (the values indicated for the number of ramifications and the number of pods relating to 100 soya plants):

|  | Control | Compound No. 2 | |
| --- | --- | --- | --- |
| Dose of active ingredient |  | 2 kg/hectare | 1 kg/hectare |
| Number of ramifications (100 plants) | 84 | 114 | 186 |
| Number of pods (100 plants) | 1,664 | 2,694 | 2,815 |
| Weight of grain collected (100 plants) | 678 g | 1,160 g | 1,390 g |
| Weight of 1,000 grains | 180 g | 226 g | 220 g |

In another experiment which was different from that described immediately above, the same method was used as in the former experiment, except that the treatment was carried out on August 30th on soya plants at the stage of six trifoliate leaves (the soya seeds having been sown on the same day as in the preceding experiment). The results observed on December 18th are reported in the table below.

|  | Control | Compound No. 2 | |
| --- | --- | --- | --- |
| Dose of active ingredient used |  | 2 kg/hectare | 1 kg/hectare |
| Number of ramifications (100 plants) | 104 | 117 | 125 |
| Number of pods (100 plants) | 2,176 | 2,651 | 2,871 |
| Weight of grain collected (100 plants) | 1,005 g | 1,303 g | 1,279 g |
| Weight of 1,000 grains | 162 g | 176 g | 172 g |

It will be observed from these experiments that the treatments carried out with compound No. 2 result in a significant increase in the soya harvest, compared with the untreated control.

These results clearly show the remarkable properties of the compounds according to the invention, which compounds can therefore be used on all kinds of monocotyledon (in particular graminaceous) and dicotyledon plants, such as those on large-scale farms (in particular, soya) and industrial farms, fruit plants, vegetable plants, ornamental plants, medicinal plants, plants grown for perfume, and the like, in order to increase yields, but also to promote ramification, modify habit, reduce size such as to obtain more compact plants, etcetera. Compounds Nos. 2, 5, 6, 7 and 10 are noted as being very especially preferred compounds.

For their use in practice, the compounds according to the invention are rarely employed by themselves. Most frequently, they form part of compositions which generally comprise, in addition to the active ingredient according to the invention, a carrier and/or a surface-active agent.

In general, these compositions contain from 0.001 to 95% by weight of active ingredient, a carrier which is acceptable in agriculture and/or from 0 to 20% of a surface-active agent.

The term "carrier", for the purpose of the present description, denotes an organic or inorganic, natural or synthetic material with which the active ingredient is combined in order to facilitate its application to the plant, to the seeds or to the soil, or in order to facilitate its transportation or handling. The carrier can be solid (e.g., clays, natural or synthetic silicates, calcium carbonate, magnesium carbonate or calcium sulfate) or liquid (e.g., water, alcohols, ketones, ethers, esters, aromatic hydrocarbons, halogenohydrocarbons or petroleum fractions).

The surface-active agent, for the purpose of the present description, can be a wetting, dispersing or emulsifying agent, which can be ionic or non-ionic. Examples which may be mentioned are nonionics, such as condensates of ethylene oxide with fatty alcohols, fatty acids, fatty amides, fatty amines or alkylphenols, fatty acid esters of sorbitol, and sucrose derivatives, anionics, such as salts of lignosulfonic acids, alkyl-arylsulfonic acids, alkyl-sulfosuccinates and -sulfosuccinamates, and amino acid derivatives, cationics, such as the acetates of alkyl-amines or of imidazoline, and amphoterics, such as alkylbetaines or sulfobetaines.

In addition to the active ingredient, the carrier and the surface-active agent, the compositions according to the invention can contain other additives, such as dispersing agents which are not surface-active, peptizing agents, protective colloids, thickeners, adhesives which increase rain resistance, stabilizers, preservatives, corrosion inhibitors, dyestuffs, sequestering agents, anti-foam agents, anti-caking agents, anti-freeze agents and the like.

The compositions according to the invention can be prepared in the form of wettable powders, soluble powders, dusting powders, granules, solutions, emulsifiable concentrates, emulsions, suspension concentrates, suspensions and dispersions.

The wettable powders are usually prepared by premixing the active ingredient with a solid carrier and wetting and dispersing agents, in the form of powders, so that they contain from 10 to 95% by weight of active ingredient and from 0.5 to 20% by weight of surface-active agents. This premix is then ground either in a mill, e.g., a pin-disc mill equipped with a powder selector, or in an "air-ject" mill, the latter apparatus being preferred for active ingredients with a low m.p.

By way of examples, the compositions of three wettable powders according to the invention are given below, the percentages being expressed by weight:

| Active ingredient (compound No. 2) | 20% | 50% | 70.0% |
| --- | --- | --- | --- |
| Sodium alkylnaphthalenesulfonate (wetting agent) | 1% | 1% | 1.5% |
| Calcium lignosulfonate (deflocculant) | 5% | 5% | 6.0% |
| Kaolin clay (inert filler) | 74% | 44% | 22.5% |

The water-soluble powders are usually obtained by mixing 20 to 95% by weight of active ingredient, 0 to 10% of an anti-caking filler and 0 to 1% of a wetting agent, the remainder consisting of a water-soluble filler which is principally a salt.

An example of the composition of a water-soluble powder is given below:

| Active ingredient (compound No. 7) | 80.0% |
| --- | --- |
| Anionic wetting agent (alkali metal alkylnaphthalenesulfonate) | 0.5% |
| Anti-caking silica | 4.0% |
| Ammonium sulfate | 15.5% |

The dusting powders can be prepared in the same fashion as the wettable powders, but without the surface-active agents, dispersing agents and protective colloids, which serve no purpose in these formulations. In this case, the solid carrier is especially selected to facilitate grinding, to absorb, if the active ingredient is liquid, and to ensure flowability.

The granules and microgranules, which generally have a low content of active ingredient, can be manufactured beforehand and then impregnated, or manufactured in bulk, e.g., by atomization or by extrusion. In the latter case, they require the addition of binders and of hygroscopic products for ensuring their rapid disintegration in the soil. They generally contain from 0.5 to 25% by weight of active ingredient and from 0 to 10% by weight of additives, such as stabilizers, slow-release modifiers, binders and solvents.

The emulsifiable concentrates contain the active ingredient dissolved in a solvent (generally an aromatic hydrocarbon) and also, where necessary, an auxiliary solvent or co-solvent, which can be a ketone, an ester, an ether or the like. They contain from 5 to 60% by weight/volume of active ingredients and from 2 to 20% by weight/volume of emulsifying agent and can be prepared, e.g., by dissolving the active ingredient, in the solvent or mixture of solvents and the emulsifier, in a vat equipped with good means for agitation and with means for circulating fluid for heating or cooling.

By way of example, the compositions of three emulsifiable concentrates according to the invention are given below:

| Active ingredient (compound No. 2) | 50 g | 100 g | 200 g |
| --- | --- | --- | --- |
| Acid phosphate of a 9:1 ethylene oxide/nonylphenol condensate | 30 g | 50 g | 100 g |
| Cyclohexanone | 200 g | 233 g | 467 g |
| Solvent (aromatic hydrocarbons) q.s.p. | 1 liter | 537 g | 202 g |

The so-called "flowable" suspension concentrates, which can also be applied by spraying, after dilution in water, are prepared such as to provide a stable fluid product which does not form a deposit. They contain from 10 to 50% by weight of active ingredient, from 0.5 to 15% by weight of surface-active agents, from 0.5 to 10% by weight of protective colloids or anti-sedimentation agents, from 0 to 10% of various additives, such as anti-foam agents, thickeners, stabilizers, adhesives and anti-freeze agents, and, as the carrier, water or an organic liquid in which the active ingredient is insoluble, or a mixture of these two. Certain organic solids or inorganic salts can be dissolved in the carrier to delay sedimentation or to act as an anti-freeze agent for the water.

These suspension concentrates can be prepared, e.g., by dispersing the pre-ground active ingredient in a liquid carrier, which can be water, a vegetable or mineral oil or an emulsified mixture of the two, containing the auxiliary ingredients, such as the viscosity regulator, the preservative and the anti-freeze agent, and then grinding the dispersion in a ball mill.

Aqueous dispersions and aqueous emulsions, e.g., compositions obtained by diluting, with water, a wettable powder or an emulsifiable concentrate according to the invention, are included in the general scope of the present invention. These emulsions can be of the water-in-oil type or of the oil-in-water type and they can have a thick consistency, such as that of a "mayonnaise".

For so-called "very low volume" application, with spraying in the form of very fine droplets, solutions in organic solvents, containing from 70 to 99% of active ingredient, are prepared.

All of the subject compositions can be applied to the plants by various methods, such as spraying onto the aerial part of the plants, soaking the seeds, the plants, the soil balls around the roots, the roots or the fruits, watering the soil, injection into the plant, and so forth.

Finally, the present invention relates to a process for modifying plant growth (i.e., for modifying the physiology of the plants in various ways), which comprises applying, to the plants, an effective amount of at least one compound according to the formula (I), or a salt of one of these compounds. The dose of active ingredient to be used can vary according to different factors, such as the type of crop to be treated, its stage of development, the climatic conditions, the nature of the land, and so forth. In practice, the treatments according to the invention are carried out by applying, to the said crops, doses of active ingredient which can range from 0.05 kg/hectare to 10 kg/hectare.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for improving soya crop plant growth, which comprises applying to a soya crop plant locus, a soya crop plant growth regulating amount of at least one compound having the structural formula:

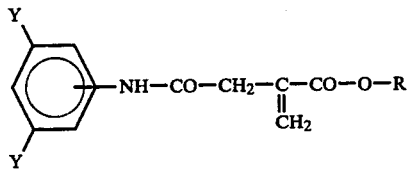

wherein R is hydrogen, an alkyl radical containing from 1 to 16 carbon atoms, an alkenyl radical containing from 3 to 15 carbon atoms or an alkynyl radical containing from 3 to 5 carbon atoms, and Y is a halogen atom, or a salt of such compound wherein R is hydrogen.

2. The method of claim 1, wherein R is hydrogen, an alkyl radical containing from 1 to 8 carbon atoms or an alkenyl radical containing from 3 to 5 carbon atoms, or an amine salt of such compound wherein R is hydrogen.

3. The method of claim 2, wherein R is an alkenyl radical containing from 3 to 5 carbon atoms.

4. The method of claim 2, wherein the compound is N-(3,5-dichlorophenyl)-2-methylene-succinamic acid.

5. The method of claim 2, wherein the compound is allyl N-(3,5-dichlorophenyl)-2-methylenesuccinamate.

6. The method of claim 2, wherein the compound is methyl N-(3,5-dichlorophenyl)-2-methylenesuccinamate.

7. The method of claim 2, wherein the compound is isopropyl N-(3,5-dichlorophenyl)-2-methylenesuccinamate.

8. The method of claim 2, wherein the compound is n-butyl N-(3,5-dichlorophenyl)-2-methylenesuccinamate.

9. The method of claim 2, wherein the compound is n-hexyl N-(3,5-dichlorophenyl)-2-methylenesuccinamate.

10. The method of claim 2, wherein the compound is ethanolamine N-(3,5-dichlorophenyl)-2-methylenesuccinamate.

11. A composition of matter for use in improving soya crop plant growth comprising (i) a non-herbicidal, soya crop plant growth regulating amount of at least one compound having the structural formula:

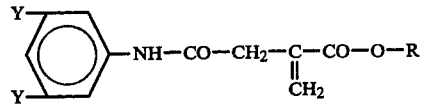

wherein R is an alkyl radical containing from 1 to 16 carbon atoms, an alkenyl radical containing from 3 to 15 carbon atoms or an alkynyl radical containing from 3 to 5 carbon atoms, and Y is a halogen atom, (ii) an agronomically acceptable inert carrier and (iii) a surface-active agent.

12. The composition of claim 11, wherein R is an alkyl radical containing from 1 to 8 carbon atoms or an alkenyl radical containing from 3 to 5 carbon atoms.

13. The composition of claim 12, wherein R is an alkenyl radical containing from 3 to 5 carbon atoms.

14. The composition of claims 11, 12 or 13, comprising from 0.001 to 95% by weight of the compound (i).

15. The composition of claim 12, wherein the compound is allyl N-(3,5-dichlorophenyl)-2-methylenesuccinamate.

16. The composition of claim 12, wherein the compound is methyl N-(3,5-dichlorophenyl)-2-methylenesuccinamate.

17. The composition of claim 12, wherein the compound is isopropyl N-(3,5-dichlorophenyl)-2-methylenesuccinamate.

18. The composition of claim 12, wherein the compound is n-butyl N-(3,5-dichlorophenyl)-2-methylenesuccinamate.

19. The composition of claim 12, wherein the compound is n-hexyl N-(3,5-dichlorophenyl)-2-methylenesuccinamate.

20. A 2-methylenesuccinamic acid derivative having the structural formula:

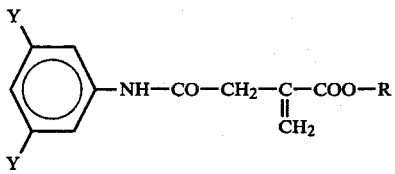

wherein R is an alkyl radical containing from 1 to 16 carbon atoms, an alkenyl radical containing from 3 to 15 carbon atoms or an alkynyl radical containing from 3 to 5 carbon atoms, and Y is a halogen atom.

21. The compound of claim 20, wherein R is an alkyl radical containing from 1 to 8 carbon atoms or an alkenyl radical containing from 3 to 5 carbon atoms.

22. The compound of claim 21, wherein R is an alkenyl radical containing from 3 to 5 carbon atoms.

23. The compound of claim 21, which is allyl N-(3,5-dichlorophenyl)-2-methylenesuccinamate.

24. The compound of claim 21, which is methyl N-(3,5-dichlorophenyl)-2-methylenesuccinamate.

25. The compound of claim 21, which is isopropyl N-(3,5-dichlorophenyl)-2-methylenesuccinamate.

26. The compound of claim 21, which is n-butyl N-(3,5-dichlorophenyl)-2-methylenesuccinamate.

27. The compound of claim 21, which is n-hexyl N-(3,5-dichlorophenyl)-2-methylenesuccinamate.

* * * * *

UNITED STATES PATENT AND TRADEMARK OFFICE
CERTIFICATE OF CORRECTION

PATENT NO. : 4,431,442
DATED : February 14, 1984
INVENTOR(S) : ANDRE DISDIER et al Page 1 of 2

It is certified that error appears in the above-identified patent and that said Letters Patent is hereby corrected as shown below:

IN THE SPECIFICATION:

Column 4, lines 51-54, kindly change the formula to read:

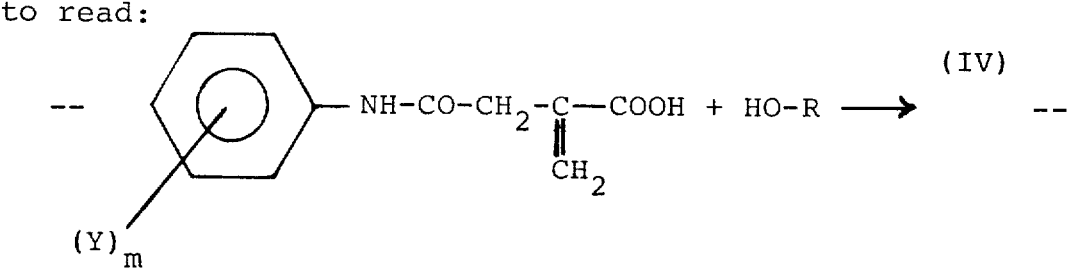

Column 4, lines 56-59, kindly change the formula to read:

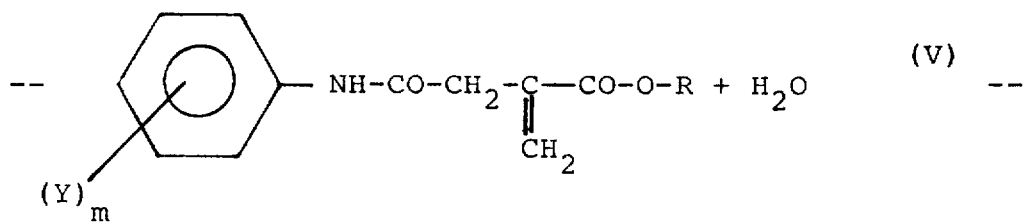

UNITED STATES PATENT AND TRADEMARK OFFICE
CERTIFICATE OF CORRECTION

PATENT NO. : 4,431,442
DATED : February 14, 1984
INVENTOR(S) : ANDRE DISDIER et al It is certified that error appears in the above-identified patent and that said Letters Patent is hereby corrected as shown below:

Column 7, lines 36-40, kindly change the formula to read:

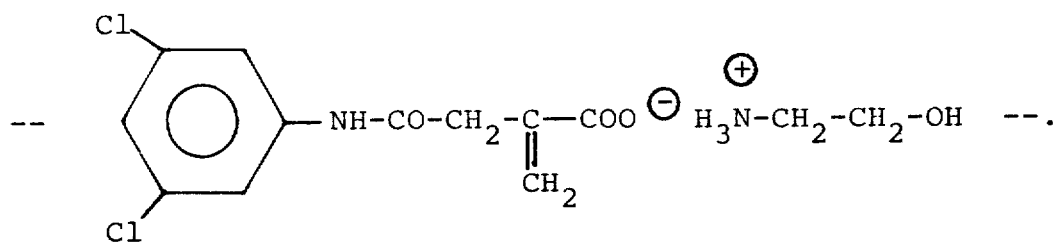

Signed and Sealed this

Ninth Day of April 1985

[SEAL]

Attest:

DONALD J. QUIGG

Attesting Officer     Acting Commissioner of Patents and Trademarks